United States Patent [19]
Yamauchi et al.

[11] Patent Number: 5,137,446
[45] Date of Patent: Aug. 11, 1992

[54] ORTHODONTIC IMPLEMENT CONTROLLABLE OF CORRECTION FORCE

[75] Inventors: Kiyoshi Yamauchi; Naoharu Yamamoto, both of Miyagi, Japan

[73] Assignee: Tokin Corporation and Tomy, Inc., Miyagi, Japan

[21] Appl. No.: 711,936

[22] Filed: Jun. 7, 1991

[30] Foreign Application Priority Data

Jun. 7, 1990 [JP] Japan .................................. 147326

[51] Int. Cl.$^5$ .................................. A61C 3/00
[52] U.S. Cl. .................................. 433/20; 433/21
[58] Field of Search .................................. 433/18, 20, 21; 148/402

[56] References Cited

U.S. PATENT DOCUMENTS

| | | | |
|---|---|---|---|
| 4,197,643 | 4/1980 | Burstone et al. | 433/20 |
| 4,337,090 | 6/1982 | Harrison | 148/402 |
| 4,780,154 | 10/1988 | Mori et al. | 148/402 X |
| 4,818,226 | 4/1989 | Berendt et al. | 433/20 |
| 4,849,032 | 7/1989 | Kawaguchi | 148/402 X |
| 4,943,326 | 7/1990 | Ozawa et al. | 148/402 X |
| 4,950,340 | 8/1990 | Wakita et al. | 148/402 |
| 5,044,947 | 9/1991 | Sachdeva et al. | 433/20 |
| 5,046,948 | 9/1991 | Miura | 433/20 X |

OTHER PUBLICATIONS

Scripta Metallurgical vol. 14, No. 8, 1980 pp. 911–914 T. Tadaki et al., Crystal Structure and Microstructure of Cold Worked TiNi Alloy with Unusual Elastic Behavior.

Primary Examiner—Robert P. Swiatek
Assistant Examiner—Nicholas D. Lucchesi
Attorney, Agent, or Firm—Hopgood, Calimafde, Kalil, Blaustein & Judlowe

[57] ABSTRACT

An orthodontic teeth alignment correction wire element made of an alloy represented by the chemical formula of $Ti_aNi_{b-c}C_c$, wherein $a+b=100$, $b=50-52$, $c=0.25-5.0$, or an alloy represented by the chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, and exhibits pseudoelasticity at the natural human body temperature. The wire has different recovery forces at different sections therealong by heat treating those sections at controlled temperatures of 400°–600° C. and for controlled time periods of 10–150 minutes and thereafter reheat treating them. An orthodontic coil is made of each of the above-described alloy wires for correction of mismatch of the upper and the lower jaws.

6 Claims, 4 Drawing Sheets

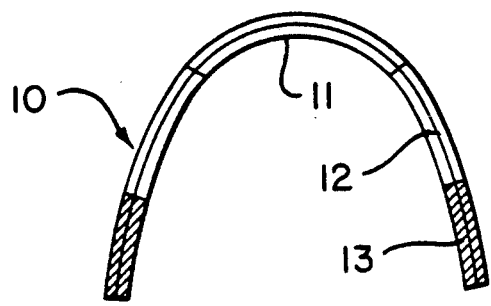
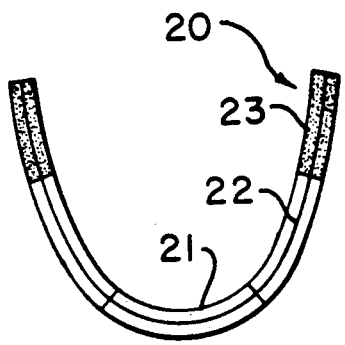
FIG. 8  FIG. 9
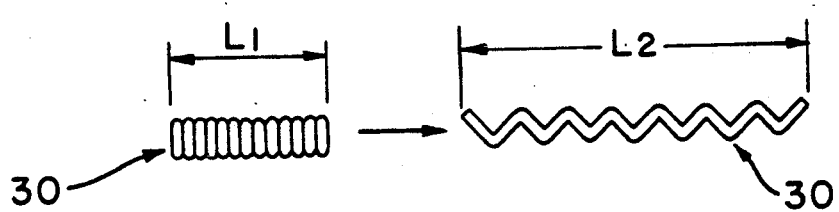
FIG. 10  FIG. 11

ORTHODONTIC IMPLEMENT CONTROLLABLE OF CORRECTION FORCE

BACKGROUND OF THE INVENTION

1. Field of the Invention

The present invention relates to orthodontic implements for use in correction of irregular and abnormal alignment of teeth and mismatching of upper and lower jaws, and in particular, to such implements using Ti-Ni alloy wire capable of generating a controlled correction force.

2. Description of the Prior Art

In order to correct the irregular alignment of teeth, an elastic wire element has usually been used as an element of the orthodontic implement. In detail, the wire element is bent in an appropriate or an ideal arch form and attached by brackets to the upper or lower teeth to move each one of the teeth due to the shape recovery force of the wire element.

As the elastic wire element, although a stainless steel wire has been conventionally used, a nitinol or Ti-Ni shape memory alloy wire has recently been used as disclosed in a paper entitled "Laboratory and clinical analyses of nitinol wire" by Andreasen et al, Am. J. Orthod. February 1978, pp 142-151 (reference 1) and another paper entitled "A clinical trial of alignment of teeth using a 0.019 inch thermal nitinol wire with a transition temperature range between 31° C. and 45° C." by Andreasen, Am. J. Orthod. November 1980, pp 528-537 Reference 2) and others.

Reference 2 discloses that nitinol wire annealed at 500° C. is different from the stainless steel wire in the springback properties and is activated by mouth heat to return to its original shape. The springback property of the Nitinol is known as a pseudoelasticity. The pseudoelasticity is referred to as an unusual elastic behavior in a paper entitled "CRYSTAL STRUCTURE AND MICROSTRUCTURE OF A COLD WORKED TiNi ALLOY WITH UNUSUAL ELASTIC BEHAVIOR" by Tadaki et al, METALLURGICA, Vol. 14, 1980, Pergamon Press Ltd. pp 911-914 (Reference 3). The cold worked TiNi alloy has the pseudoelasticity and is used for the orthodontic wire element.

In correction of teeth alignment, the desired correction force is not constant for all of the teeth. In detail, providing that the desired force is one (1) for incisors of the maxillary or the upper jaw, correction forces of 1.5, 1.5, and 3.8 are desired for canines, premolars and first molars of the maxillary, respectively, and 0.7, 1.1, 1.1 and 3.2 are desired for incisors canines premolars and first molars of mandible or the lower jaw of a patient, respectively.

A typical desired correction force is about 80 grams for the incisors.

When a single orthodontic wire element is used for correction of the upper or lower teeth, it is difficult to adjust the correction force to a desired one for each one of the teeth. Accordingly, it is difficult to reduce the patient's discomfort. Also, to use different wires for different sections of teeth becomes complicated.

As another aspect of the orthodontics, it is known that a coil spring is used for correction of mismatching of the maxillary and the mandible. The coil connects the maxillary with the mandible so that the coil moves them in correct occlusal relation due to the elasticity. If the coil spring is strong, it increases the patient's discomfort, but if it is weak, correction is not sufficiently effected. Further, since the coil is subjected to a large number of repetitions of expansion and contraction, it is desirable to have high durability in order to withstand the repetition of expansion and contraction.

SUMMARY OF INVENTION

Therefore, it is an object of the present invention to provide an orthodontic implement capable of reducing the patient's discomfort without adversely affecting correction.

It is another object of the present invention to provide an orthodontic implement as a wire element which is capable of generating correction forces desired for teeth located at different positions.

It is further object of the present invention to provide an orthodontic implement as a coil spring which has a sufficiently high durability to withstand repetition of expansion and contraction.

According to the present invention, an orthodontic implement for use in correction of an irregular and abnormal alignment of teeth comprises a wire of an alloy represented by the chemical formula of $Ti_aNi_{b-c}C_c$, wherein $a+b=100$, $b=50-55$, $c=0.25-5.0$, said wire having a pseudoelasticity at the natural human body temperature, said pseudoelasticity being controllable in its shape recovery stress by heat treating the wire at a controlled temperature of 400°-600° C. and for a controlled time period of 10-150 minutes.

Another orthodontic implement according to the present invention comprises a wire of an alloy represented by the chemical formula of $Ti_aNi_{b-c-d}C_cX_d$, wherein X is at least one element selected from V, Cr, Fe, Nb, Ta, W, and Al, wherein $a+b=100$, $b=50-55$, $c=0.25-5.0$, $d=0.25-2.0$, said wire exhibiting pseudoelasticity at the natural human body temperature, said pseudoelasticity being controllable in its shape recovery stress by heat treating said wire at a controlled temperature of 400°-600° C. and for a controlled time period of 10-150 minutes.

According to the present invention, an orthodontic wire element is made of an alloy represented by the chemical formula of $Ti_aNi_{b-c}C_c$, $a+b=100$, $b=50-52$, $c=0.25-5.0$, said wire having a pseudoelasticity at the natural human body temperature, said pseudoelasticity being different in its shape recovery stress at different sections therealong.

Another orthodontic wire element is made of an alloy represented by the chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, said wire having a pseudoelasticity at the natural human body temperature, said pseudoelasticity being different in its shape recovery stress at different sections therealong.

According to the present invention, an orthodontic implement for use in correction of mismatch between the upper and the lower jaws of a patient is also provided which comprises a coil element made of an alloy wire represented by a chemical formula of $Ti_aNi_{b-c}C_c$, wherein $a+b=100$, $b=50-55$, $c=0.25-5.0$, said wire having high durability and pseudoelasticity at the natural human body temperature, said pseudoelasticity being controllable in its shape recovery stress by heat treating the alloy wire at a controlled temperature of 400°-600° C. and for a controlled time period of 10-150 minutes.

Another orthodontic implement for use in correction of mismatch between the upper and the lower jaws of a patient comprises a coil element made of an alloy wire represented by a chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, said wire exhibiting high durability and pseudoelasticity at the natural human body temperature, said pseudoelasticity being controllable in its shape recovery stress by heat treating the alloy wire at a controlled temperature of 400°-600° C. and for a controlled time period of 10-150 minutes.

BRIEF DESCRIPTION OF THE DRAWINGS

FIG. 8 is an orthodontic wire element for the upper teeth according to an embodiment of the present invention;

FIG. 9 is an orthodontic wire element for the lower teeth according to another embodiment of the present invention;

FIG. 10 and 11 are views illustrating a contraction state and an expansion state of an orthodontic coil element according to another embodiment of the present invention.

DESCRIPTION OF PREFERRED EMBODIMENTS

For the orthodontic implement according to the present invention, a wire is used which is made of an alloy represented by a chemical formula of $Ti_aNi_{b-c}C_c$, wherein $a+b=100$, $b=50-52$, $c=0.25-5.0$. The alloy wire exhibits pseudoelasticity at the natural human body temperature and the pseudoelasticity is controlled by heat treatment so that the wire can be different in its shape recovery stress or force at different sections therealong.

The addition of C (carbon) to the TiNi alloy lowers the austenitic and martensitic transition temperatures by producing TiC in the alloy. In addition to this, it serves to elevate the unloaded shape recovery stress within the pseudoelasticity range. To this end, the amount of C is 0.25 at% or more. When it exceeds 5 at%, the cold working of the resultant alloy is almost impossible. Therefore, the amount of C is limited 5 at% or less.

Another alloy, which is obtained by replacement of a part of Ti and Ni of the above described Ti-Ni-C alloy by V, Cr, Fe, Nb, Ta, W, and Al, can be used for the orthodontic implement similar to the above-described Ti-Ni-C alloy. The resultant alloy is represented by a chemical formula of $Ti_aNi_{b-c-d}C_cX_d$, wherein X is at least one element selected from V, Cr, Fe, Nb, Ta, W, and Al, wherein $a+b=100$, $b=50-55$, $c=0.25-5.0$, $d=0.25-2.0$.

Now, examples of the above-described alloys will be described below as regards pseudoelasticity in comparison with the conventional Ti-Ni shape memory alloy.

EXAMPLES

Alloy $Ti_{49.5}Ni_{50}C_{0.50}$ (alloy A) $Ti_{49.5}Ni_{49}C_{0.5}V_{1.0}$ (Alloy B) $Ti_{49.3}Ni_{50.7}$ (Alloy C) were prepared by the melt method using a high frequency induction vacuum furnace. The ingots were formed into wires with a diameter of 1.3 mm by hot and cold working. The wires were then subjected to a solution treatment at 950° C. for 10 minutes. Thereafter, the wires were cold-worked into wires with a diameter of 1.0 mm (40% cold reduction). A plurality of sample wires were cut from the resultant wires and were annealed at 500° C. for various periods. Then, each of the sample wires was subjected to a tension test of a load-unload cycle at 37° C. (which is about the natural human body temperature) for the maximum strain $\epsilon=5\%$ in order to obtain a stress-strain curve.

Figure 1:
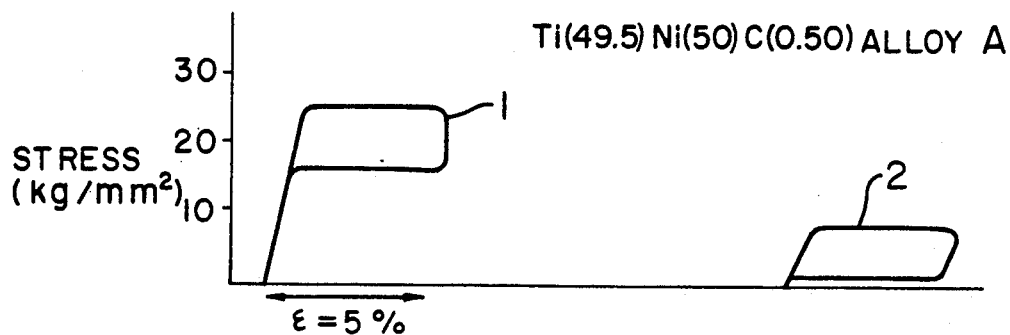
FIG. 1 is a graph illustrating stress-strain curves of $Ti_{49.5}Ni_{50}C_{0.50}$ alloy wires annealed at different heat treatment conditions.

FIG. 1 shows the stress-strain curves of sample wires of alloy A, Curve 1 being a typical one of samples of wires annealed for 30 minutes or less, Curve 2 being a typical one of the samples of wires annealed for 100 minutes or more.

Figure 2:
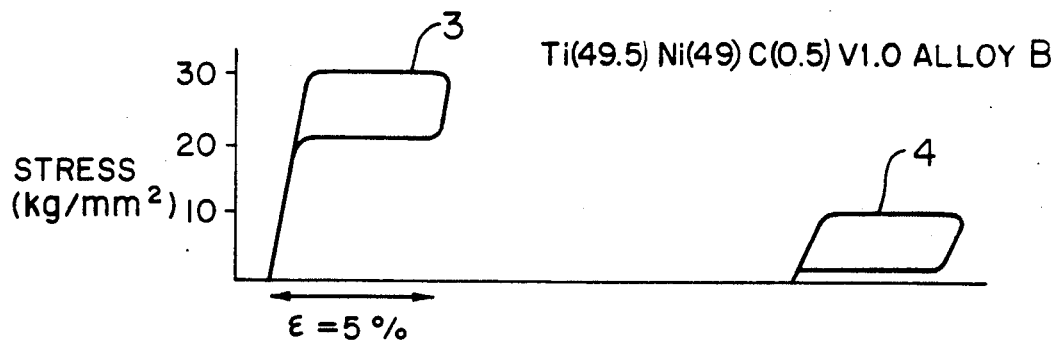
FIG. 2 is a graph illustrating stress-strain curves of $Ti_{49.5}Ni_{49}C_{0.5}V_{1.0}$ alloy wires annealed at different heat treatment conditions.

FIG. 2 shows stress-strain curves of sample wires of alloy B. Curve 3 is for a sample wire annealed for 10 minutes and Curve 4 is for one annealed for 150 minutes.

Figure 3:
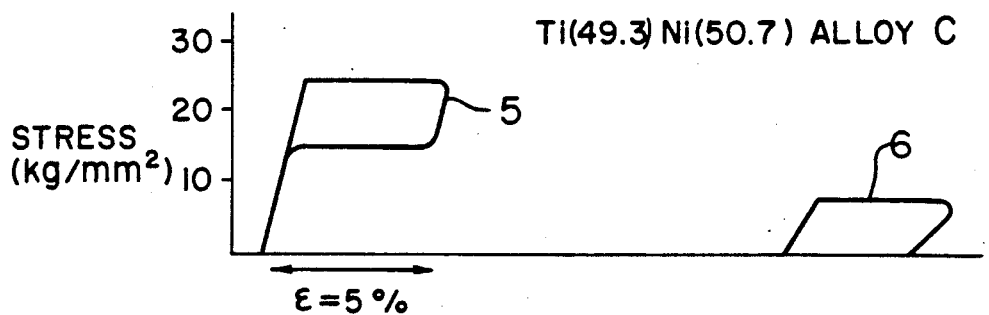
FIG. 3 is a graph illustrating stress-strain curves of $Ti_{49.3}Ni_{50.7}$ alloy wires annealed at different heat treatment conditions.

FIG. 3 shows stress-strain curves 5 and 6 of sample wires of alloy C annealed for 10 and 150 minutes, respectively.

It is seen from FIGS. 1 and 2 that wires of alloys A and B have the pseudoelasticity even at different annealing time periods within a range of 10-150 minutes. The stress level of the pseudoelasticity is high and low when the annealing time period is short and long, respectively. Therefore, the stress levels of the pseudoelasticity can be controlled by changing the annealing time period at a constant annealing temperature.

In comparison with this, it is seen from FIG. 3 (Alloy C) that the pseudoelasticity disappears by annealing for 150 minutes and that the residual strain is caused even when the stress is removed.

Wire samples (a diameter of 0.45 mm) of each of alloys A and B were also annealed at 500° C. for 130 minutes (condition I) and then subjected to a bend test of a load-unload cycle. In the bend test, the sample wire was supported at two supporting points which were separated by 50 mm from each other. The load was applied to the middle point of the wire between said supporting points. A distance pushed down by the load was measured as the strain.

Figure 4:
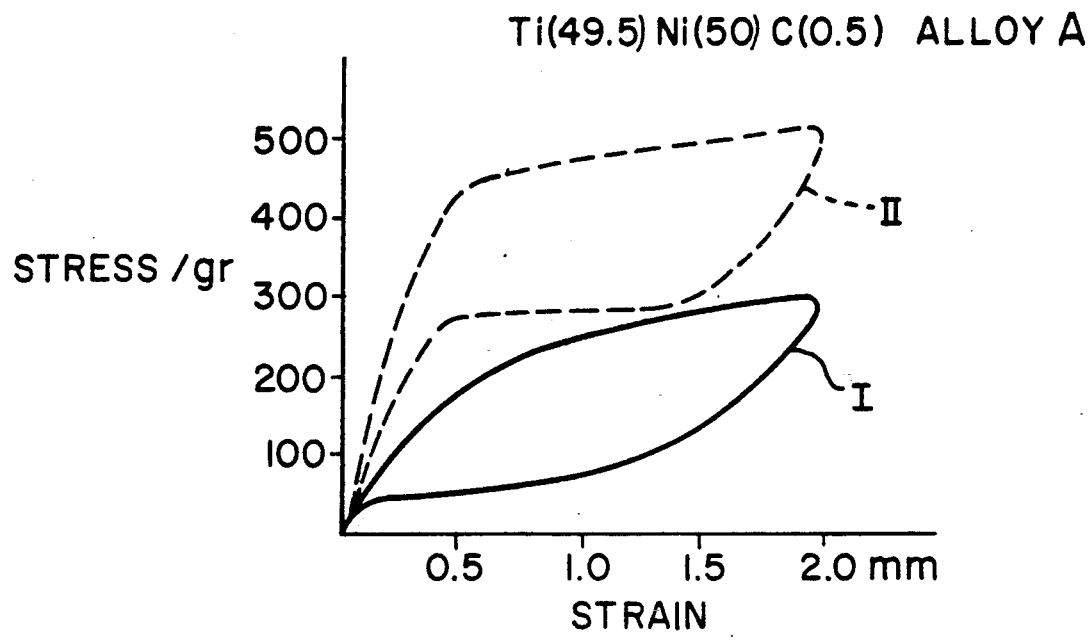
FIG. 4 is an enlarged graph illustrating stress-strain curves of $Ti_{49.5}Ni_{50}C_{0.50}$ alloy wires annealed at different heat treatment conditions.
Figure 5:
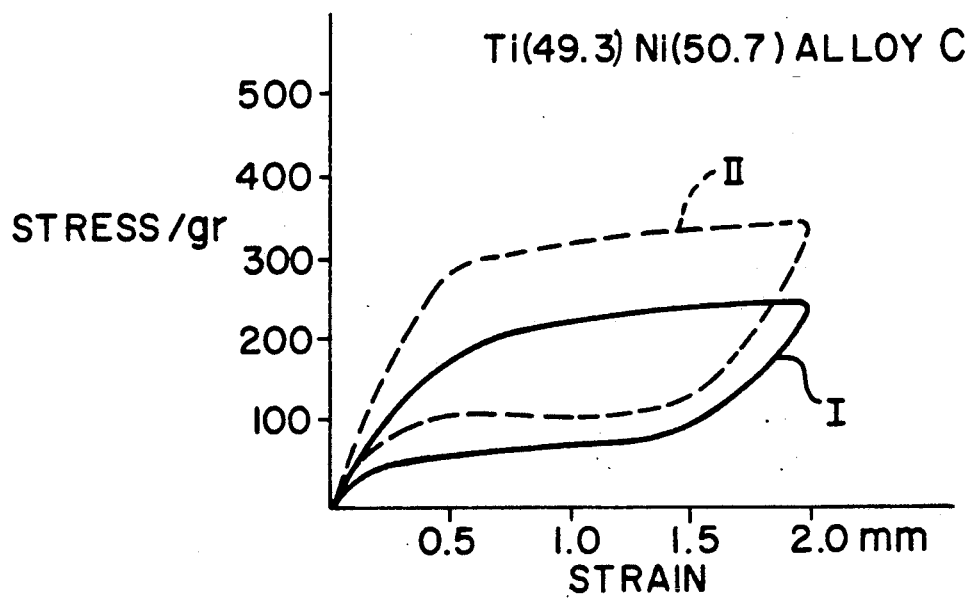
FIG. 5 is an enlarged graph illustrating stress-strain curves of $Ti_{49.3}Ni_{50.7}$ annealed at different heat treatment conditions.

Thereafter, the sample wires were again heat treated at 430° C. for 1 minute (condition II), and then subjected to the similar bend test. The results are shown in FIGS. 4 and 5 where a solid line I and a dotted line II represent the results under the annealing conditions I and II, respectively. It is understood from FIG. 4 and FIG. 5 that the stress level of the pseudoelasticity of alloy A can be sufficiently changed by reheat treatment in comparison with Alloy C.

Figure 6:
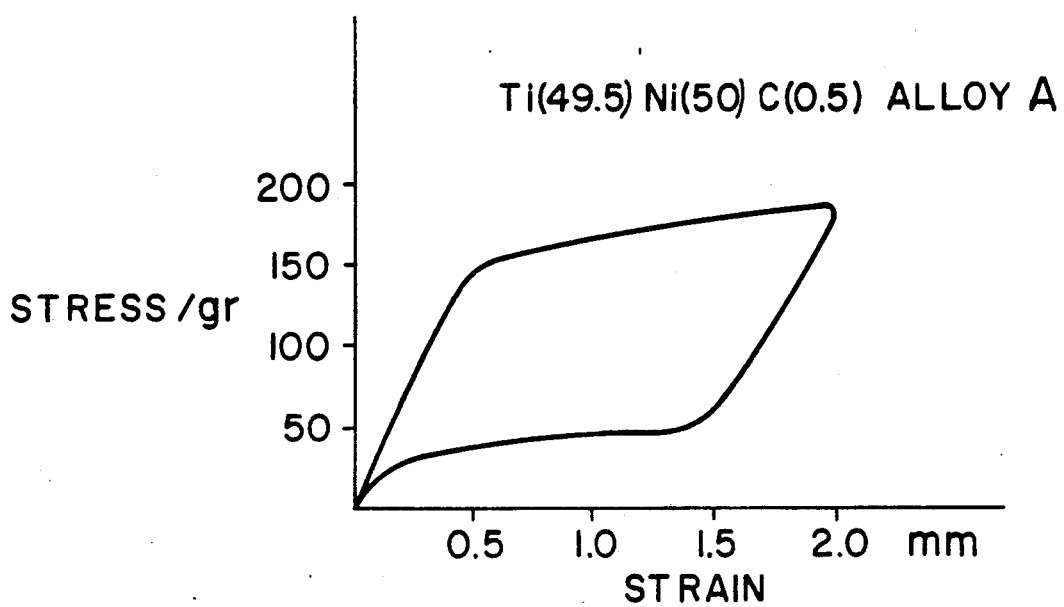
FIG. 6 is a graph illustrating a stress-strain curve of $Ti_{49.5}Ni_{50}C_{0.50}$ alloy wire annealed at 500° C. for 150 minutes.
Figure 7:
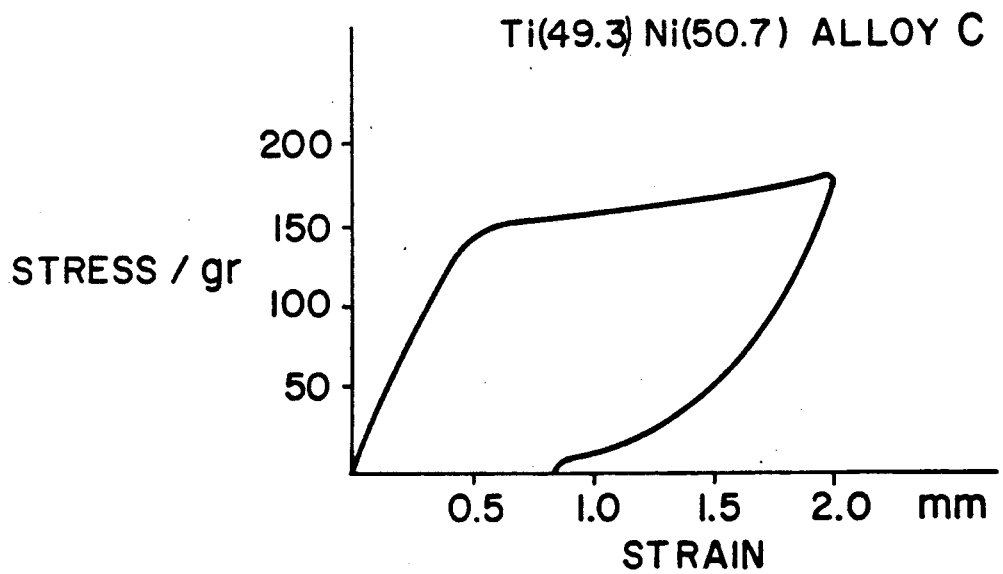
FIG. 7 is a graph illustrating a stress-strain curve of $Ti_{49.3}Ni_{50.7}$ annealed at the heat treatment condition similar to FIG. 6.

Similar sample wires were annealed at 500° C. for 150 minutes and then subjected to the similar bend test. The resultant stress-strain curves are shown in FIGS. 6 and 7. The pseudoelasticity can be obtained in the sample of alloy A but is not obtained in the sample of alloy C.

It is understood from the above examples that the wires of alloys A and B can be controlled in the stress level of the pseudoelasticity by control of the annealing condition and by reheat treatment. In application of the wires onto orthodontics, the shape recovery force or stress under unload is used for correction of the teeth alignment. As will be understood from the above examples, the unloaded shape recovery stress can also be controlled by control of the annealing condition.

It should be noted that the similar control of the unloaded shape recovery stress level can be realized in the alloys generally represented by the chemical formulae as described above.

Wires of these alloys can also be controlled to be different in the unloaded shape recovery stress at different sections therealong by changing the annealing condition for those sections.

Referring to FIG. 8, an orthodontic wire element 10 for the upper teeth according to an embodiment shown therein is made from alloy A and is formed in the ideal arch form. The wire element has different correction forces at different sections, that is, at the incisors section 11, at the canines and premolars section 12, and at the molars section 13 by changing the annealing condition and/or the reheat treatment condition for these sections. The ratio of the correction forces at the sections 11, 12, and 13 is selected to be 1:1.5:3.8.

Referring to FIG. 9, another orthodontic wire element 20 for the lower teeth shown therein comprises the incisors section 21, the canines and premolars section 22, and the molars section 23. The ratio of the correction forces at the sections 11, 12, and 13 is selected 0.7:1.1:3.2, in relation to the correction force of the incisors section 11 for the upper teeth.

Referring to FIG. 10, a coil spring 30 was formed of a wire (with a diameter of 0.25 mm) of alloy A for correction of mismatch of the upper and the lower jaws. The wire was annealed at 500° C. for 30 minutes to have an appropriate unloaded shape recovery stress level so as to reduce the patient's discomfort. The coil spring 30 has an outer diameter 0.75 mm at the contraction state.

The coil spring 30 was subjected to a durability test for expansion (FIG. 11) and contraction at about 37° C. and a number of expansion and contraction is counted until the coil spring is damaged. The test was repeated by changing the expansion to contraction ratio (L2 to L1).

In comparison, a similar coil spring was formed of a wire of alloy C and was subjected to the similar test.

The result of the tests are shown in the following table.

TABLE

| L2/L1 | COIL OF ALLOY A | COIL OF ALLOY C |
|---|---|---|
| 2 | 100,000 | 100,000 |
| 3 | 13,000 | 8,000 |
| 4 | 5,000 | 2,000 |
| 5 | 500 | 50 |
| 6 | 30 | 10 |

It will be seen from the table that the coil spring according to the present invention is superior in durability to the coil spring made of the conventional TiNi alloy.

WHAT IS CLAIMED IS:

1. An orthodontic implement for use in correction of an irregular and abnormal alignment of teeth which comprises a wire of an alloy represented by a chemical formula of $Ti_aNi_{b-c}C_c$, wherein $a+b=100$, $b=50-52$, $c=0.25-5.0$, said wire having a pseudoelasticity at the natural human body temperature, said pseudoelasticity being controllable in its shape recovery stress by heat treating at a controlled temperature of 400°-600° C. and for a controlled time period of 10-150 minutes.

2. An orthodontic implement for use in correction of an irregular and abnormal alignment of teeth which comprises a wire of an alloy represented by a chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, said wire having a pseudoelasticity at the natural human body temperature, said pseudoelasticity being controllable in its shape recovery stress by heat treating at a controlled temperature of 400°-600° C. and for a controlled time period of 10-150 minutes.

3. An orthodontic wire element for use in correction of an irregular and abnormal alignment of teeth which is made of an alloy represented by a chemical formula of $Ti_aNi_{b-c}C_c$, wherein $a+b=100$, $b=50-52$, $c=0.25-5.0$, said wire having a pseudoelasticity at the natural human body temperature, said pseudoelasticity being different in its shape recovery stress at different sections therealong.

4. An orthodontic wire element for use in correction of an irregular and abnormal alignment of teeth which is made of an alloy represented by a chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, said wire having a pseudoelasticity at the natural human body temperature, said pseudoelasticity being different in its shape recovery stress at different sections therealong.

5. An orthodontic implement for use in correction of mismatch between the upper and the lower jaws of a patient which comprises a coil element made of an alloy wire represented by a chemical formula of $Ti_aNi_{b-c}C_c$, wherein $a+b=100$, $b=50-52$, $c=0.25-5.0$, said wire having a high durability and having pseudoelasticity at the natural human body temperature, said pseudoelasticity being controllable in its shape recovery stress by heat treating at a controlled temperature of 400°-600° C. and for a controlled time period of 10-150 minutes.

6. An orthodontic implement for use in correction of mismatch between the upper and the lower jaws of a patient which comprises a coil element made of an alloy wire represented by a chemical formula of $Ti_aNi_{b-c-d}C_cX_d$, wherein X is at least one element selected from V, Cr, Fe, Nb, Ta, W, and Al, wherein $a+b=100$, $b=50-52$, $c=0.25-5.0$, $d=0.25-2.0$, said wire having high durability and pseudoelasticity at the natural human body temperature, said pseudoelasticity being controllable in its shape recovery stress by heat treating said wire at a controlled temperature of 400°-600° C. and for a controlled time period of 10-150 minutes.

* * * * *

UNITED STATES PATENT AND TRADEMARK OFFICE
CERTIFICATE OF CORRECTION

PATENT NO. : 5,137,446
DATED : August 11, 1992
INVENTOR(S) : Yamauchi, et al

It is certified that error appears in the above-indentified patent and that said Letters Patent is hereby corrected as shown below:

On the title page, item [54] and Column 1, line 2,

Delete "Controllable of Correction Force".

item [30] "Foreign Application Priority Data"
should read -- Jun. 7, 1990  [JP]  Japan . . . . . 2-147326--

Signed and Sealed this

Twenty-fifth Day of June, 1996

Attest:

BRUCE LEHMAN

Attesting Officer     Commissioner of Patents and Trademarks